(12) United States Patent
Nagata

(10) Patent No.: US 10,844,024 B1
(45) Date of Patent: Nov. 24, 2020

(54) METHOD FOR PRODUCING THIOCARBOXAMIDINE SALT COMPOUND

(71) Applicant: KUMIAI CHEMICAL INDUSTRY CO., LTD., Tokyo (JP)

(72) Inventor: Toshihiro Nagata, Tokyo (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 16/958,225

(22) PCT Filed: Dec. 26, 2018

(86) PCT No.: PCT/JP2018/047744
§ 371 (c)(1),
(2) Date: Jun. 26, 2020

(87) PCT Pub. No.: WO2019/131715
PCT Pub. Date: Jul. 4, 2019

(30) Foreign Application Priority Data

Dec. 27, 2017 (JP) .................... 2017-251100

(51) Int. Cl.
*C07D 261/04* (2006.01)
(52) U.S. Cl.
CPC .................. *C07D 261/04* (2013.01)
(58) Field of Classification Search
CPC .................................... C07D 261/04
USPC ....................................... 548/243
See application file for complete search history.

(56) References Cited

U.S. PATENT DOCUMENTS

| | | | |
|---|---|---|---|
| 2004/0110749 A1 | 6/2004 | Nakatani et al. | |
| 2007/0185334 A1 | 8/2007 | Uchida | |
| 2008/0275249 A1 | 11/2008 | Uchida | |
| 2012/0264947 A1 | 10/2012 | Frasetto | |

FOREIGN PATENT DOCUMENTS

| | | |
|---|---|---|
| JP | 2005-232042 A | 9/2005 |
| JP | 2013-512201 A | 4/2013 |
| WO | 2002/062770 A1 | 8/2002 |
| WO | 2005/095352 A1 | 10/2005 |
| WO | 2006/068092 A1 | 6/2006 |

OTHER PUBLICATIONS

International Search Report dated Feb. 5, 2019, issued in counterpart application No. PCT/JP2018/047744, w/English translation (5 pages).
Written Opinion dated Feb. 5, 2019, issued in counterpart application No. PCT/JP2018/047744 (4 pages).
Decision to Grant a Patent dated Jan. 23, 2020, issued in counterpart Japanese Patent Application No. 2019-562074, w/English translation (5 pages).

*Primary Examiner* — Kristin A Vajda
(74) *Attorney, Agent, or Firm* — Westerman, Hattori, Daniels & Adrian, LLP

(57) ABSTRACT

The present disclosure provides an industrially preferable, economical, and environmentally friendly method for producing a compound [C1] of formula (5), namely, a (4,5-dihydroisoxazol-3-yl)thiocarboxamidine salt compound. The present disclosure relates to a method wherein: a reaction expressed by reaction formula [C2] is caused so as to produce a compound of formula (4) by reacting a compound of formula (3) with a halogenation agent in the presence of a nitrile solvent, and the compound of formula (4) is subsequently reacted with an isothiouronium-forming agent, thereby producing a compound of formula (5).

[C1]

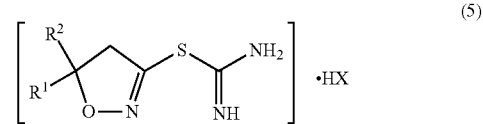

[C2]

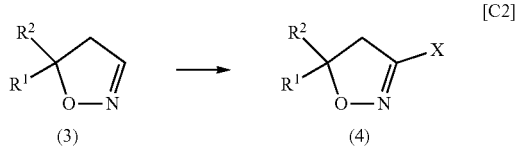

25 Claims, No Drawings

METHOD FOR PRODUCING THIOCARBOXAMIDINE SALT COMPOUND

TECHNICAL FIELD

The present invention relates to a process for producing a compound of the formula (5):

[Chemical Formula 1]

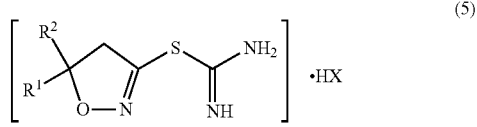

wherein $R^1$, $R^2$ and X are as described below, i.e., a (4,5-dihydroisoxazol-3-yl)thiocarboxamidine salt compound.

BACKGROUND ART (4,5-Dihydroisoxazol-3-yl)thiocarboxamidine salt compounds of the formula (5) are useful as intermediates for the production of pharmaceuticals, agricultural chemicals, etc.

WO 2002/062770 (Patent Document 1) discloses useful herbicides. Among them, pyroxasulfone is well known as a herbicide having excellent herbicidal activity. Furthermore, J P 2013-512201 A (Patent Document 2) and WO 2006/068092 (Patent Document 3) disclose that the compounds of the formula (5) are important intermediates for the herbicides described in Patent Document 1.

JP 2013-512201 A (Patent Document 2) discloses a process for producing (4,5-dihydroisoxazol-3-yl)thiocarboxamidine salt compounds. In the specific and most preferable process described in Patent Document 2, a 3-unsubstituted-4,5-dihydroisoxazole compound is reacted with a halogenating agent (e.g., a chlorinating agent) with use of tert-butanol as a reaction solvent to produce a 3-halogenated-4,5-dihydroisoxazole compound (e.g., 3-chloro-4,5-dihydroisoxazole compound), which is then reacted with thiourea in the same reaction solvent to obtain a target (4,5-dihydroisoxazol-3-yl)thiocarboxamidine salt compound (for example, see Example 6 of Patent Document 2).

WO 2006/068092 (Patent Document 3) discloses a process for producing a (4,5-dihydroisoxazol-3-yl)thiocarboxamidine salt compound by reacting a 3-halogenated-4,5-dihydroisoxazole compound with thiourea in the presence of an acid. In particular, Patent Document 3 describes that an acid is effective. That is, according to Patent Document 3, an acid is essential for the reaction of a 3-halogenated-4,5-dihydroisoxazole compound with thiourea. The acid may be in a catalytic amount, but it is understood that a certain amount of acid is required to obtain a high yield in a short reaction time (see, for example, Examples 4 and 5 of Patent Document 3).

JP 2013-512201 A (Patent Document 2) describes that the process of Patent Document 2 does not require additional addition of an acid (see Patent Document 2, paragraph 0064). In the process of Patent Document 2, the 3-chloro-4,5-dihydroisoxazole compound is produced by reacting the 3-unsubstituted-4,5-dihydroisoxazole compound with chlorine, and then the reaction with thiourea is performed directly without performing purification in the same reaction vessel, that is, in a one-pot process (see, for example, Example 6 and paragraph 0060 of Patent Document 2). After the chlorination, if the reaction with thiourea is performed in a one-pot process without performing purification, the hydrogen chloride generated by the chlorination remains in the reaction system without being removed, and is presumed to serve as an acid catalyst in the reaction with thiourea. Therefore, additional addition of an acid before the reaction with thiourea is not necessary in the process of Patent Document 2.

[Chemical Formula 2]

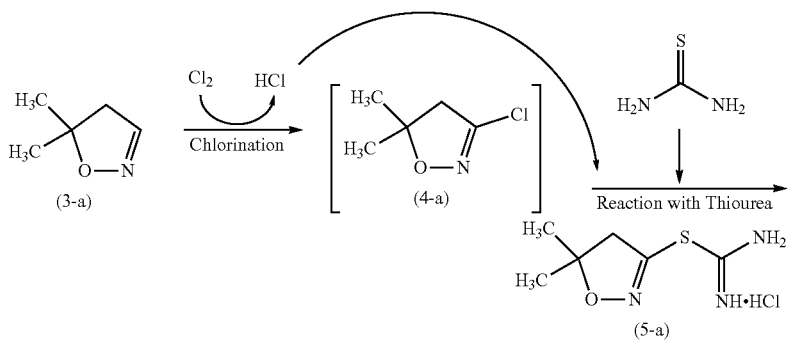

The process of Patent Document 2 does not require the additional addition of an acid, but an acid itself is essential also in the reaction with thiourea in the process of Patent Document 2, and as the acid, an acid generated by chlorination in the previous step and remaining is understood to be utilized (see the above FIGURE).

However, in Example 6 of Patent Document 2, a long reaction time of 60 hours or more at a reaction temperature of 20° C. is required to complete the reaction. From the viewpoint of economic efficiency, etc., it is generally preferable that the reaction be completed at around ambient temperature and in a short time, but it is understood that the process of Patent Document 2 requires a long reaction time at around ambient temperature. Long reaction times are not economical and are industrially undesirable. Further, the yield achieved in Example 6 of Patent Document 2 is only 59%, and the process of Patent Document 2 is not economical in terms of yield and is not industrially preferable.

CITATION LIST

Patent Document

Patent Document 1: WO 2002/062770 A1
Patent Document 2: JP 2013-512201 A
Patent Document 3: WO 2006/068092 A1

SUMMARY OF INVENTION

Technical Problem

There has been desired an industrially preferable process for producing a compound of the above formula (5), i.e., a target (4,5-dihydroisoxazol-3-yl)thiocarboxamidine salt compound, the process being capable of solving the above-described one or more disadvantages or problems in the prior art. Therefore, an object of the present disclosure is to provide a process for producing the target compound, which process is industrially preferable, economical, and environmentally friendly. A specific object of the present disclosure is to provide a process capable of producing the target compound in a short time and with a high yield. Another specific object of the present disclosure is to provide a process capable of producing the target compound by a simple operation without requiring a special equipment.

Solution to Problem

In view of the circumstances as described above, the present inventor has earnestly studied a process for producing a compound of the formula (5). As a result, the present inventor unexpectedly found that the above problems can be solved by providing the following processes for producing the compound of the formula (5). The present inventor has accomplished the present invention based on this finding.

That is, in one embodiment, the present invention is as follows.

[I-1] A process for producing a compound of the formula (5):

[Chemical Formula 1]

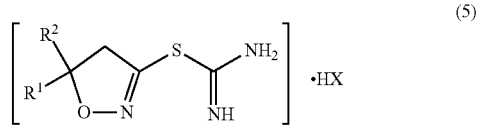

(5)

wherein $R^1$ and $R^2$ are each independently optionally substituted (C1-C6)alkyl; optionally substituted (C3-C6)cycloalkyl; optionally substituted (C2-C6)alkenyl; optionally substituted (C2-C6)alkynyl; optionally substituted (C1-C6)alkoxy; or optionally substituted phenyl; or $R^1$ and $R^2$, together with the carbon atom to which they are attached form a 4- to 12-membered carbocyclic ring, wherein the formed ring is optionally substituted, X is a halogen, which comprises the following steps (C) and (D):

step (C): reacting a compound of the formula (3) with a halogenating agent in the presence of a nitrile solvent to produce a compound of the formula (4),

[Chemical Formula 2]

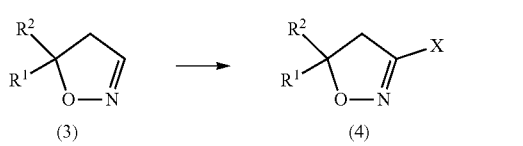

wherein $R^1$, $R^2$ and X are as defined above, step (D): reacting the compound of the formula (4) with an isothiouronium-forming agent to produce the compound of the formula (5),

[Chemical Formula 3]

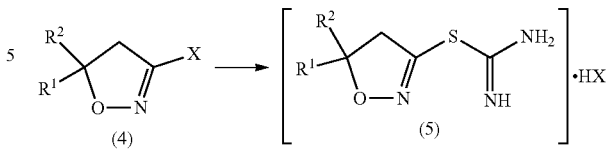

wherein $R^1$, $R^2$ and X are as defined above.

[I-2] The process according to [I-1], wherein the reaction of the step (C) is performed in the presence of a nitrile solvent and a water solvent.

[I-3] The process according to [I-1] or [I-2], wherein the amount of the nitrile solvent to be used in the reaction of the step (C) is 0.4 to 2.0 L based on 1 mol of the compound of the formula (3).

[I-4] The process according to [I-1] or [I-2], wherein the amount of the nitrile solvent to be used in the reaction of the step (C) is 0.5 to 1.5 L based on 1 mol of the compound of the formula (3).

[I-5] The process according to [I-1] or [I-2], wherein the amount of the nitrile solvent to be used in the reaction of the step (C) is 0.5 to 1.0 L based on 1 mol of the compound of the formula (3).

[I-6] The process according to any one of [I-2] to [I-5], wherein the amount of the water solvent to be used in the reaction of the step (C) is 0.10 to 0.40 L based on 1 mol of the compound of the formula (3).

[I-7] The process according to any one of [I-2] to [I-5], wherein the amount of the water solvent to be used in the reaction of the step (C) is 0.15 to 0.33 L based on 1 mol of the compound of the formula (3).

[I-8] The process according to any one of [I-2] to [I-7], wherein the amount of water to be used in the reaction of the step (C) is 10 vol % or more and 42 vol % or less of the amount of the mixed solvent of the nitrile solvent and water.

[I-9] The process according to any one of [I-2] to [I-7], wherein the amount of water to be used in the reaction of the step (C) is 10 vol % or more and 40 vol % or less of the amount of the mixed solvent of the nitrile solvent and water.

[I-10] The process according to any one of [I-2] to [I-7], wherein the amount of water to be used in the reaction of the step (C) is 20 vol % or more and 40 vol % or less of the amount of the mixed solvent of the nitrile solvent and water.

[I-11] The process according to any one of [I-1] to [I-10], wherein the reaction of the step (D) is performed in the presence of a nitrile solvent.

[I-12] The process according to any one of [I-1] to [I-10], wherein the reaction of the step (D) is performed in the presence of a nitrile solvent and a water solvent.

[I-13] The process according to [I-11] or [I-12], wherein the amount of the nitrile solvent to be used in the reaction of the step (D) is 0.4 to 2.0 L based on 1 mol of the compound of the formula (3).

[I-14] The process according to [I-11] or [I-12], wherein the amount of the nitrile solvent to be used in the reaction of the step (D) is 0.5 to 1.5 L based on 1 mol of the compound of the formula (3).

[I-15] The process according to [I-11] or [I-12], wherein the amount of the nitrile solvent to be used in the reaction of the step (D) is 0.5 to 1.0 L based on 1 mol of the compound of the formula (3).

[I-16] The process according to any one of [I-12] to [I-15], wherein the amount of the water solvent to be used in the reaction of the step (D) is 0.10 to 0.40 L based on 1 mol of the compound of the formula (3).

[I-17] The process according to any one of [I-12] to [I-15], wherein the amount of the water solvent to be used in the reaction of the step (D) is 0.15 to 0.33 L based on 1 mol of the compound of the formula (3).

[I-18] The process according to any one of [I-12] to [I-17], wherein the amount of water to be used in the reaction of the step (D) is 10 vol % or more and 42 vol % or less of the amount of the mixed solvent of the nitrile solvent and water.

[I-19] The process according to any one of [I-12] to [I-17], wherein the amount of water to be used in the reaction of the step (D) is 10 vol % or more and 40 vol % or less of the amount of the mixed solvent of the nitrile solvent and water.

[I-20] The process according to any one of [I-12] to [I-17], wherein the amount of water to be used in the reaction of the step (D) is 20 vol % or more and 40 vol % or less of the amount of the mixed solvent of the nitrile solvent and water.

[I-21] The process according to any one of [I-1] to [I-20], wherein the reaction of the step (C) and the reaction of the step (D) are performed in the same solvent.

[I-22] The process according to any one of [I-1] to [I-21], wherein the step (C) and the step (D) are performed in the same reaction vessel.

[I-23] The process according to any one of [I-1] to [I-22], wherein the nitrile solvent is acetonitrile.

[I-24] The process according to any one of [I-1] to [I-23], wherein the halogenating agent is chlorine.

[I-25] The process according to any one of [I-1] to [I-24], wherein the isothiouronium-forming agent is thiourea.

[I-26] The process according to any one of [I-1] to [I-25], wherein $R^1$ and $R^2$ are methyl and X is a chlorine atom.

[I-27] The process according to any one of [I-1] to [I-26], wherein the reaction of the step (C) is performed at −5° C. to 50° C.

[I-28] The process according to any one of [I-1] to [I-26], wherein the reaction of the step (C) is performed at 0° C. to 30° C.

[I-29] The process according to any one of [I-1] to [I-28], wherein the reaction of the step (D) is performed at 0° C. to 60° C.

[I-30] The process according to any one of [I-1] to [I-28], wherein the reaction of the step (D) is performed at 15° C. to 40° C.

In another embodiment, the present invention is as follows.

[II-1] A process for producing a compound of the formula (5):

[Chemical Formula 11]

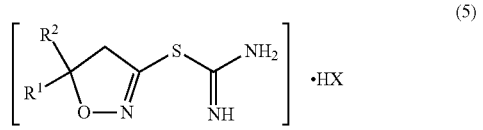

wherein $R^1$ and $R^2$ are each independently optionally substituted (C1-C6)alkyl; optionally substituted (C3-C6)cycloalkyl; optionally substituted (C2-C6)alkenyl; optionally substituted (C2-C6)alkynyl; optionally substituted (C1-C6)alkoxy; or optionally substituted phenyl; or $R^1$ and $R^2$, together with the carbon atom to which they are attached form a 4- to 12-membered carbocyclic ring, wherein the formed ring is optionally substituted, and X is a halogen, which comprises the following steps (C) and (D):

step (C): reacting a compound of the formula (3) with a halogenating agent in the presence of a nitrile solvent and a water solvent to produce a compound of the formula (4),

[Chemical Formula 12]

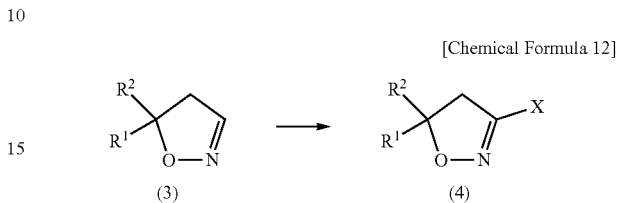

wherein $R^1$, $R^2$ and X are as defined above, step (D): reacting the compound of the formula (4) with an isothiouronium-forming agent to produce the compound of the formula (5),

[Chemical Formula 13]

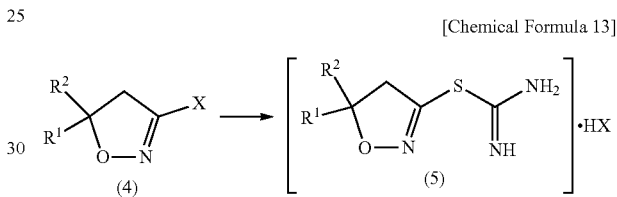

wherein $R^1$, $R^2$ and X are as defined above.

[II-2] The process according to [II-1], wherein the amount of the nitrile solvent to be used in the reaction of the step (C) is 0.1 to 5.0 L based on 1 mol of the compound of the formula (3).

[II-3] The process according to [II-1], wherein the amount of the nitrile solvent to be used in the reaction of the step (C) is 0.3 to 3.0 L based on 1 mol of the compound of the formula (3).

[II-4] The process according to [II-1], wherein the amount of the nitrile solvent to be used in the reaction of the step (C) is 0.4 to 2.0 L based on 1 mol of the compound of the formula (3).

[II-5] The process according to [II-1], wherein the amount of the nitrile solvent to be used in the reaction of the step (C) is 0.5 to 2.0 L based on 1 mol of the compound of the formula (3).

[II-6] The process according to [II-1], wherein the amount of the nitrile solvent to be used in the reaction of the step (C) is 0.4 to 1.5 L based on 1 mol of the compound of the formula (3).

[II-7] The process according to [II-1], wherein the amount of the nitrile solvent to be used in the reaction of the step (C) is 0.5 to 1.5 L based on 1 mol of the compound of the formula (3).

[II-8] The process according to [II-1], wherein the amount of the nitrile solvent to be used in the reaction of the step (C) is 0.5 to 1.0 L based on 1 mol of the compound of the formula (3).

[II-9] The process according to any one of [II-1] to [II-8], wherein the amount of the water solvent to be used in the reaction of the step (C) is 0.10 to 1.00 L based on 1 mol of the compound of the formula (3).

[II-10] The process according to any one of [II-1] to [II-8], wherein the amount of the water solvent to be used in the reaction of the step (C) is 0.10 to 0.40 L based on 1 mol of the compound of the formula (3).
[II-11] The process according to any one of [II-1] to [II-8], wherein the amount of the water solvent to be used in the reaction of the step (C) is 0.13 to 0.40 L based on 1 mol of the compound of the formula (3).
[II-12] The process according to any one of [II-1] to [II-8], wherein the amount of the water solvent to be used in the reaction of the step (C) is 0.15 to 0.40 L based on 1 mol of the compound of the formula (3).
[II-13] The process according to any one of [II-1] to [II-8], wherein the amount of the water solvent used in the reaction of the step (C) is 0.15 to 0.33 L based on 1 mol of the compound of the formula (3).
[II-14] The process according to any one of [II-1] to [II-8], wherein the amount of the water solvent to be used in the reaction of the step (C) is 0.13 to 0.35 L based on 1 mol of the compound of the formula (3).
[II-15] The process according to any one of [II-1] to [II-14], wherein the amount of water to be used in the reaction of the step (C) is 5 vol % or more and 50 vol % or less of the amount of the mixed solvent of the nitrile solvent and water.
[II-16] The process according to any one of [II-1] to [II-14], wherein the amount of water to be used in the reaction of the step (C) is 10 vol % or more and 42 vol % or less of the amount of the mixed solvent of the nitrile solvent and water.
[II-17] The process according to any one of [II-1] to [II-14], wherein the amount of water to be used in the reaction of the step (C) is 10 vol % or more and 40 vol % or less of the amount of the mixed solvent of the nitrile solvent and water.
[II-18] The process according to any one of [II-1] to [II-14], wherein the amount of water to be used in the reaction of the step (C) is 20 vol % or more and 40 vol % or less of the amount of the mixed solvent of the nitrile solvent and water.
[II-19] The process according to any one of [II-1] to [II-14], wherein the amount of water to be used in the reaction of the step (C) is 20 vol % or more and 30 vol % or less of the amount of the mixed solvent of the nitrile solvent and water.
[II-20] The process according to any one of [II-1] to [II-14], wherein the amount of water to be used in the reaction of the step (C) is 10 vol % or more and 30 vol % or less of the amount of the mixed solvent of the nitrile solvent and water.
[II-21] The process according to any one of [II-1] to [II-20], wherein the reaction of the step (D) is performed in the presence of a nitrile solvent and a water solvent.
[II-22] The process according to [II-21], wherein the amount of the nitrile solvent to be used in the reaction of the step (D) is 0.1 to 5.0 L based on 1 mol of the compound of the formula (3).
[II-23] The process according to [II-21], wherein the amount of the nitrile solvent to be used in the reaction of the step (D) is 0.3 to 3.0 L based on 1 mol of the compound of the formula (3).
[II-24] The process according to [II-21], wherein the amount of the nitrile solvent to be used in the reaction of the step (D) is 0.4 to 2.0 L based on 1 mol of the compound of the formula (3).
[II-25] The process according to [II-21], wherein the amount of the nitrile solvent to be used in the reaction of the step (D) is 0.5 to 2.0 L based on 1 mol of the compound of the formula (3).
[II-26] The process according to [II-21], wherein the amount of the nitrile solvent to be used in the reaction of the step (D) is 0.4 to 1.5 L based on 1 mol of the compound of the formula (3).
[II-27] The process according to [II-21], wherein the amount of the nitrile solvent to be used in the reaction of the step (D) is 0.5 to 1.5 L based on 1 mol of the compound of the formula (3).
[II-28] The process according to [II-21], wherein the amount of the nitrile solvent to be used in the reaction of the step (D) is 0.5 to 1.0 L based on 1 mol of the compound of the formula (3).
[II-29] The process according to any one of [II-21] to [II-28], wherein the amount of the water solvent to be used in the reaction of the step (D) is 0.10 to 1.00 L based on 1 mol of the compound of the formula (3).
[II-30] The process according to any one of [II-21] to [II-28], wherein the amount of the water solvent to be used in the reaction of the step (D) is 0.10 to 0.40 L based on 1 mol of the compound of the formula (3).
[II-31] The process according to any one of [II-21] to [II-28], wherein the amount of the water solvent to be used in the reaction of the step (D) is 0.13 to 0.40 L based on 1 mol of the compound of the formula (3).
[II-32] The process according to any one of [II-21] to [II-28], wherein the amount of the water solvent to be used in the reaction of the step (D) is 0.15 to 0.40 L based on 1 mol of the compound of the formula (3).
[II-33] The process according to any one of [II-21] to [II-28], wherein the amount of the water solvent to be used in the reaction of the step (D) is 0.15 to 0.33 L based on 1 mol of the compound of the formula (3).
[II-34] The process according to any one of [II-21] to [II-28], wherein the amount of the water solvent to be used in the reaction of the step (D) is 0.13 to 0.35 L based on 1 mol of the compound of the formula (3).
[II-35] The process according to any one of [II-21] to [II-34], wherein the amount of water to be used in the reaction of the step (D) is 5 vol % or more and 50 vol % or less of the amount of the mixed solvent of the nitrile solvent and water.
[II-36] The process according to any one of [II-21] to [II-34], wherein the amount of water to be used in the reaction of the step (D) is 10 vol % or more and 42 vol % or less of the amount of the mixed solvent of the nitrile solvent and water.
[II-37] The process according to any one of [II-21] to [II-34], wherein the amount of water to be used in the reaction of the step (D) is 10 vol % or more and 40 vol % or less of the amount of the mixed solvent of the nitrile solvent and water.
[II-38] The process according to any one of [II-21] to [II-34], wherein the amount of water to be used in the reaction of the step (D) is 20 vol % or more and 40 vol % or less of the amount of the mixed solvent of the nitrile solvent and water.
[II-39] The process according to any one of [II-21] to [II-34], wherein the amount of water to be used in the reaction of the step (D) is 20 vol % or more and 30 vol % or less of the amount of the mixed solvent of the nitrile solvent and water.
[II-40] The process according to any one of [II-21] to [II-34], wherein the amount of water to be used in the reaction of the step (D) is 10 vol % or more and 30 vol % or less of the amount of the mixed solvent of the nitrile solvent and water.
[II-41] The process according to any one of [II-1] to [II-40], wherein the reaction of the step (C) and the reaction of the step (D) are performed in the same solvent.
[II-42] The process according to any one of [II-1] to [II-41], wherein the step (C) and the step (D) are performed in the same reaction vessel.
[II-43] The process according to any one of [II-1] to [II-42], wherein the nitrile solvent is acetonitrile.
[II-44] The process according to any one of [II-1] to [II-43], wherein the halogenating agent is a chlorinating agent or a brominating agent.

[II-45] The process according to any one of [II-1] to [II-43], wherein the halogenating agent is chlorine or bromine.
[II-46] The process according to [II-44] or [II-45], wherein $R^1$ and $R^2$ are each independently (C1-C4)alkyl and X is a chlorine atom or a bromine atom.
[II-47] The process according to [II-44] or [II-45], wherein $R^1$ and $R^2$ are methyl and X is a chlorine atom or a bromine atom.
[II-48] The process according to any one of [II-1] to [II-43], wherein the halogenating agent is a chlorinating agent.
[II-49] The process according to any one of [II-1] to [II-43], wherein the halogenating agent is chlorine.
[II-50] The process according to [II-48] or [II-49], wherein $R^1$ and $R^2$ are each independently (C1-C4)alkyl and X is a chlorine atom.
[II-51] The process according to [II-48] or [II-49], wherein $R^1$ and $R^2$ are methyl and X is a chlorine atom.
[II-52] The process according to any one of [II-1] to [II-51], wherein the isothiouronium-forming agent is thiourea.
[II-53] The process according to any one of [II-1] to [II-52], wherein the reaction of the step (C) is performed at −5° C. to 50° C.
[II-54] The process according to any one of [II-1] to [II-52], wherein the reaction of the step (C) is performed at 0° C. to 30° C.
[II-55] The process according to any one of [II-1] to [II-54], wherein the reaction of the step (D) is performed at 0° C. to 60° C.
[II-56] The process according to any one of [II-1] to [II-54], wherein the reaction of the step (D) is performed at 15° C. to 40° C.

Advantageous Effects of Invention

The present disclosure provides a novel process for producing the compound of the formula (5). According to the present disclosure, there is provided a process for producing the compound of the formula (5), which can overcome one or more of the disadvantages or problems of the prior art described above.

According to the present disclosure, the target compound can be produced in a short time and with a high yield. According to the present disclosure, it is possible to produce the target compound by a simple operation without requiring a special equipment.

Therefore, the process of the present disclosure is industrially preferable, economical, and environmentally friendly, and has high industrial utility value.

DESCRIPTION OF EMBODIMENTS

The present invention will be described in detail below.
The terms and symbols used herein will be explained below.

Examples of the halogen atom include fluorine atom, chlorine atom, bromine atom and iodine atom.

(Ca-Cb) means that the number of carbon atoms is a to b. For example, "(C1-C4)" in "(C1-C4)alkyl" means that the number of the carbon atoms in the alkyl is 1 to 4.

Herein, it is to be understood that generic terms such as "alkyl" include both the straight chain and branched chain such as butyl and tert-butyl. However, when a specific term such as "butyl" is used, it is specific for "normal butyl", i.e., "n-butyl". In other words, the specific term "butyl" refers to "normal butyl", which is a straight chain. Branched chain isomers such as "tert-butyl" are referred to specifically when intended.

The prefixes "n-", "s-" and "sec-", "i-", "t-" and "tert-", "neo-", "c-" and "cyc-", "o-", "m-", and "p-" have their common meanings as follows: normal, secondary ("s-" and "sec-"), iso, tertiary ("t-" and "tert-"), neo, cyclo ("c-" and "cyc-"), ortho, meta, and para.

Herein, the following abbreviations may be used:
"Me" means methyl.
"Et" means ethyl.
"Pr", "n-Pr" and "Pr-n" mean propyl (i.e., normal propyl).
"i-Pr" and "Pr-i" mean isopropyl.
"Bu", "n-Bu" and "Bu-n" mean butyl (i.e., normal butyl).
"s-Bu" and "Bu-s" mean sec-butyl.
"i-Bu" and "Bu-i" mean isobutyl.
"t-Bu" and "Bu-t" mean tert-butyl.
"Pen", "n-Pen" and "Pen-n" mean pentyl (i.e., normal pentyl).
"Hex", "n-Hex" and "Hex-n" mean hexyl (i.e., normal hexyl).
"Dec", "n-Dec" and "Dec-n" mean decyl (i.e., normal decyl).
"c-Pr" and "Pr-c" mean cyclopropyl.
"c-Bu" and "Bu-c" mean cyclobutyl.
"c-Pen" and "Pen-c" mean cyclopentyl.
"c-Hex" and "Hex-c" mean cyclohexyl.
"Ph" means phenyl.
"Bn" means benzyl.
"Ms" means methylsulfonyl ($CH_3SO_2$—).
"Ts" means tosyl (4-$CH_3$—$C_6H_4SO_2$—).
"Tf" means trifluoromethylsulfonyl ($CF_3SO_2$—).
"Ac" means acetyl ($CH_3CO$—).

The (C1-C6)alkyl means a straight or branched alkyl having 1 to 6 carbon atoms. Examples of the (C1-C6)alkyl include, but are not limited to, methyl, ethyl, propyl, isopropyl, butyl, sec-butyl, isobutyl, tert-butyl, pentyl, isopentyl, neopentyl, and hexyl.

The (C1-C4)alkyl means a straight or branched alkyl having 1 to 4 carbon atoms. Examples of the (C1-C4)alkyl are appropriate examples of the above-mentioned examples of the (C1-C6)alkyl.

The (C1-C6)haloalkyl means a straight or branched alkyl having 1 to 6 carbon atoms which is substituted with 1 to 13 same or different halogen atoms, wherein the halogen atoms have the same meaning as defined above. Examples of the (C1-C6)haloalkyl include, but are not limited to, fluoromethyl, difluoromethyl, trifluoromethyl, chlorodifluoromethyl, 2-fluoroethyl, 2-chloroethyl, 2,2,2-trifluoroethyl, pentafluoroethyl, 3-fluoropropyl, 3-chloropropyl, 2,2,3,3,3-pentafluoropropyl, 2,2,2-trifluoro-1-trifluoromethylethyl, heptafluoropropyl, 1,2,2,2-tetrafluoro-1-trifluoromethylethyl, 4-fluorobutyl, 4-chlorobutyl, 4-bromobutyl, 2,2,3,3,4,4,4-heptafluorobutyl, 5-fluoropenty, and 6-fluorohexyl.

The (C1-C4)haloalkyl means a straight or branched alkyl having 1 to 4 carbon atoms which is substituted with 1 to 9 same or different halogen atoms, wherein the halogen atoms have the same meaning as defined above. Examples of the (C1-C4)haloalkyl include, but are not limited to, appropriate examples of the above-mentioned examples of the (C1-C6) haloalkyl.

The (C3-C6)cycloalkyl means a cycloalkyl having 3 to 6 carbon atoms. Examples of the (C3-C6)cycloalkyl are cyclopropyl, cyclobutyl, cyclopentyl, and cyclohexyl.

The (C2-C6)alkenyl means a straight or branched alkenyl having 2 to 6 carbon atoms. Examples of the (C2-C6)alkenyl include, but are not limited to, vinyl, 1-propenyl, isopropenyl, 2-propenyl, 1-butenyl, 1-methyl-1-propenyl, 2-methyl-1-propenyl, 2-butenyl, 1,3-butadienyl, 1-pentenyl, and 1-hexenyl.

The (C2-C4)alkenyl means a straight or branched alkenyl having 2 to 4 carbon atoms. Examples of the (C2-C4)alkenyl include, but are not limited to, appropriate examples of the above-mentioned examples of the (C2-C6)alkenyl.

The (C2-C6)alkynyl means a straight or branched alkynyl having 2 to 6 carbon atoms. Examples of the (C2-C6)alkynyl include, but are not limited to, ethynyl, 1-propynyl, 2-propynyl, 1-butynyl, 1-methyl-2-propynyl, 2-butynyl, 1-pentynyl, and 1-hexynyl.

The (C2-C4)alkynyl means a straight or branched alkynyl having 2 to 4 carbon atoms. Examples of the (C2-C4)alkynyl include, but are not limited to, appropriate examples of the above-mentioned examples of the (C2-C6)alkynyl.

The (C1-C6)alkoxy means a (C1-C6)alkyl-O—, wherein the (C1-C6)alkyl moiety has the same meaning as defined above. Examples of the (C1-C6)alkoxy include, but are not limited to, methoxy, ethoxy, propoxy, isopropoxy, butoxy, sec-butoxy, isobutoxy, tert-butoxy, pentyloxy, isopentyloxy, neopentyloxy, and hexyloxy.

The (C1-C4)alkoxy means a (C1-C4)alkyl-O—, wherein the (C1-C4)alkyl moiety has the same meaning as defined above. Examples of the (C1-C4)alkoxy include, but are not limited to, appropriate examples of the above-mentioned examples of the (C1-C6)alkoxy.

The cyclic hydrocarbon group means a cyclic group which is aromatic or non-aromatic and is monocyclic or multicyclic, wherein all of the ring-constituting atoms are carbon atoms.

In one embodiment, examples of the cyclic hydrocarbon group include, but are not limited to, a 3- to 14-membered (preferably 5- to 14-membered, more preferably 5- to 10-membered) cyclic hydrocarbon group which is aromatic or non-aromatic and is monocyclic, bicyclic or tricyclic. In another embodiment, examples of the cyclic hydrocarbon group include, but are not limited to, a 4- to 8-membered (preferably 5- to 6-membered) cyclic hydrocarbon group which is aromatic or non-aromatic and is monocyclic or bicyclic (preferably monocyclic).

Examples of the cyclic hydrocarbon group include, but are not limited to, cycloalkyls and aryls.

The aryls are aromatic cyclic groups among the cyclic hydrocarbon groups as defined above.

The cyclic hydrocarbon group as defined or exemplified above may include a non-condensed cyclic group (e.g., a monocyclic group or a spirocyclic group) and a condensed cyclic group, when possible.

The cyclic hydrocarbon group as defined or exemplified above may be unsaturated, partially saturated or saturated, when possible.

The cyclic hydrocarbon group as defined or exemplified above is also referred to as a carbocyclic ring group.

The carbocyclic ring is a ring which corresponds to the cyclic hydrocarbon group as defined or exemplified above.

Herein, there are no particular limitations on the "substituent(s)" for the phrase "optionally substituted" as long as they are chemically acceptable and exhibit the effects of the present invention.

Herein, examples of the "substituent(s)" for the phrase "optionally substituted" include, but are not limited to, one or more substituents (preferably 1 to 4 substituents) selected independently from Substituent Group (a).

Substituent Group (a) is a group comprising a halogen atom; a nitro group; a cyano group; a hydroxy group; an amino group; (C1-C6)alkyl; (C1-C6)haloalkyl; (C3-C6)cycloalkyl; (C2-C6)alkenyl; (C2-C6)alkynyl; (C1-C6)alkoxy; phenyl; and phenoxy.

In addition, one or more substituents (preferably 1 to 4 substituents) selected independently from Substituent Group (a) may each independently have one or more substituents (preferably 1 to 4 substituents) selected independently from Substituent Group (b).

In this context, Substituent Group (b) is the same as Substituent Group (a).

Herein, a compound having isomers includes all of the isomers and any mixture thereof in any ratio. For example, xylene includes o-xylene, m-xylene, p-xylene and any mixture thereof in any ratio. For example, dichlorobenzene includes o-dichlorobenzene, m-dichlorobenzene, p-dichlorobenzene and any mixture thereof in any ratio.

The process of the present invention includes, in one embodiment, the following scheme, wherein $R^1$, $R^2$ and X are as defined in [1].

[Chemical Formula 21]

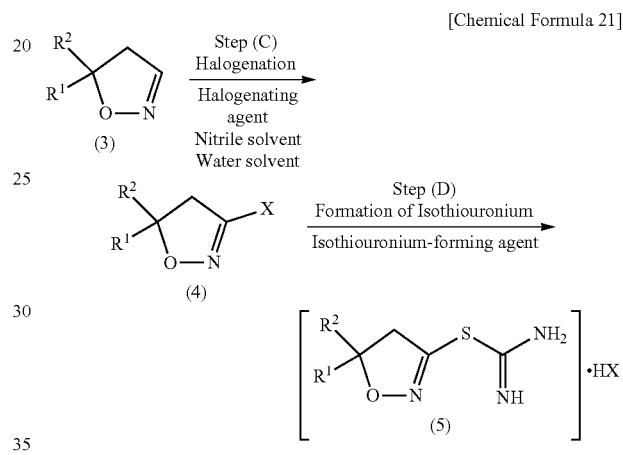

(Step (C))

The step (C) will be described.

The reaction of the step (C) is halogenation (preferably, chlorination).

The step (C) is a step of producing a compound of the formula (4), that is, a 3-halogenated-4,5-dihydroisoxazole compound (preferably, a 3-chloro-4,5-dihydroisoxazole compound) by reacting a compound of the formula (3), that is, a 3-unsubstituted-4,5-dihydroisoxazole compound, with a halogenating agent (preferably, a chlorinating agent) in the presence of a nitrile solvent. The 3-halogenated-4,5-dihydroisoxazole compound is also referred to as a 3-halogeno-4,5-dihydroisoxazole compound. In other words, the step (C) is a step of producing a compound of the formula (4) by halogenating (preferably, chlorinating) a compound of the formula (3) in the presence of a nitrile solvent.

[Chemical Formula 22]

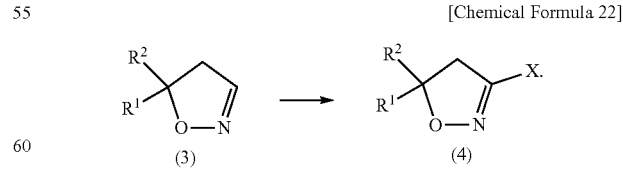

In the formula, $R^1$, $R^2$ and X are as defined above.

(Raw Material in Step (C); Compound of Formula (3))

A compound of the formula (3) is used as a raw material in the step (C). The compound of the formula (3) may be a known compound or may be produced from a known compound according to a known process. Specific examples of the compound of the formula (3) include, but are not limited thereto; 5,5-dimethyl-4,5-dihydroisoxazole, 5-ethyl-5-methyl-4,5-dihydroisoxazole, 5,5-diethyl-4,5-dihydroisoxazole, 5-isopropyl-5-methyl-4,5-dihydroisoxazole, 5-(tert-butyl)-5-methyl-4,5-dihydroisoxazole, 5-(chloromethyl)-5-methyl-4,5-dihydroisoxazole, 5-methyl-5-(trifluoromethyl)-4,5-dihydroisoxazole, 5-cyclopropyl-5-methyl-4,5-dihydroisoxazole, 5-oxa-6-azaspiro[3.4]oct-6-ene, 1-methyl-2-methyl[4.4]non-2-ene, 1-methyl-2-methyl[4.5]dec-2-ene, 5-butyl-5-methyl-4,5-dihydroisoxazole, 5-methyl-5-(4-methylpent-3-en-1-yl)-4,5-dihydroisoxazole, 5-methyl-5-(4-methylpentyl)-4,5-dihydroisoxazole, 4'H-spiro[fluorene-9,5'-isoxazole], 5,5-diphenyl-4,5-dihydroisoxazole, 5,5-bis(4-methylphenyl)-4,5-dihydroisoxazole, 5,5-bis(4-methoxyphenyl)-4,5-dihydroisoxazole, 5,5-bis(4-chlorophenyl)-4,5-dihydroisoxazole, 5-methyl-5-phenyl-4,5-dihydroisoxazole, 5-ethyl-5-phenyl-4,5-dihydroisoxazole, 5-(4-methylphenyl)-5-methyl-4,5-dihydroisoxazole, 5-(4-methoxyphenyl)-5-methyl-4,5-dihydroisoxazole, and 5-(4-chlorophenyl)-5-methyl-4,5-dihydroisoxazole. From the viewpoint of the usefulness of a product, etc., preferable specific examples of the compound of the formula (3) include 5,5-dimethyl-4,5-dihydroisoxazole, 5-ethyl-5-methyl-4,5-dihydroisoxazole, and 5,5-diethyl-4,5-dihydroisoxazole, more preferably 5,5-dimethyl-4,5-dihydroisoxazole.

(Halogenating Agent in Step (C))

The halogenating agent to be used in the step (C) may be any halogenating agent as long as the reaction proceeds. Examples of halogenating agents that can be used in the step (C) include chlorinating agents and brominating agents, preferably chlorinating agents.

(Chlorinating Agent in Step (C))

The chlorinating agents to be used in the step (C) may be any chlorinating agent as long as the reaction proceeds. Examples of chlorinating agents that can be used in the step (C) include, but are not limited to, chlorine (i.e., chlorine molecule; $Cl_2$, in other words, elemental chlorine), sulfuryl chloride, N-chloroimides (e.g., N-chlorosuccinimide and 1,3-dichloro-5,5-dimethylhydantoin), hypochlorite esters (e.g., tert-butyl hypochlorite). From the viewpoints of reactivity, selectivity, economic efficiency, etc., a preferable example of the chlorinating agent in the step (C) is chlorine (that is, chlorine molecule; $Cl_2$).

The chlorinating agent in the step (C) may be used alone or in combination of two or more kinds in any ratio. The form of the chlorinating agent in the step (C) may be any form as long as the reaction proceeds. The form of the chlorinating agent in the step (C) can be appropriately selected by a person skilled in the art.

When chlorine (that is, chlorine molecule; $Cl_2$) is used as the chlorinating agent in the step (C), the form may be any form as long as the reaction proceeds. Examples of the form include gas and liquid, preferably gas. Thus, for example, chlorine gas or liquefied chlorine, preferably chlorine gas is used.

The amount of the chlorinating agent used in the step (C) can be appropriately adjusted by a person skilled in the art. However, when chlorine (that is, chlorine molecule; $Cl_2$; preferably, chlorine gas) is used as the chlorinating agent in the step (C), the amount of the agent used may be any amount as long as the reaction proceeds. Meanwhile, from the viewpoint of yield, suppression of by-product formation, economic efficiency, etc., the amount may be, for example, in the range of 0.5 to 2.0 mol, preferably 0.9 to 2.0 mol, more preferably 0.9 to 1.5 mol, and even more preferably 1.0 to 1.2 mol based on 1 mol of the compound of the formula (3). Also when the other chlorinating agent described above is used, the same examples of the amount thereof can be mentioned.

(Brominating Agent in Step (C))

The brominating agents to be used in the step (C) may be any brominating agent as long as the reaction proceeds. Examples of brominating agents that can be used in the step (C) include, but are not limited to, bromine (i.e., bromine molecule; $Br_2$, in other words, elemental bromine) and N-bromoimides (e.g., N-bromosuccinimide, etc.).

The brominating agent in the step (C) may be used alone or in combination of two or more kinds in any ratio. The form of the brominating agent in the step (C) may be any form as long as the reaction proceeds. The form of the brominating agent in the step (C) can be appropriately selected by a person skilled in the art. The amount of the brominating agent used in the step (C) can be appropriately adjusted by a person skilled in the art.

(Solvent in Step (C))

From the viewpoints of smooth progress of the reaction, etc., it is preferable to perform the reaction of the step (C) in the presence of a solvent. From the viewpoint of yield, suppression of by-products, reactivity, economic efficiency, etc., the reaction of the step (C) is preferably performed in the presence of a nitrile solvent, and more preferably the reaction of the step (C) is performed in the presence of a nitrile solvent and a water solvent. As long as the reaction proceeds, a solvent other than the nitrile solvent and the water solvent may be used in combination. As to examples of the solvent other than the nitrile solvent and the water solvent, reference can be made to appropriate examples of the examples of the solvent that can be used in the step (D) described later. As long as the reaction proceeds, the solvent either may form a single layer or may be separated into two layers, but preferably forms a uniform single layer.

As long as the reaction proceeds, examples of the nitrile solvent in the step (C) include, but are not limited to, acetonitrile, propionitrile, etc., and any combination thereof in any ratio. However, from the same viewpoints as described above, the preferable nitrile solvent is acetonitrile.

Accordingly, from the viewpoints of yield, suppression of by-products, reactivity, economic efficiency, etc., preferable examples of the reaction solvent in the step (C) include nitriles (e.g., acetonitrile and propionitrile), water, and any combination thereof in any ratio. A more preferable example is a mixed solvent of acetonitrile and water (i.e., aqueous acetonitrile). The effect of the nitrile solvent (preferably, acetonitrile; more preferably, aqueous acetonitrile) is explained by working examples below. In addition, from the viewpoint of ease of handling and recycling, it was unexpectedly found during the investigation of the present invention that the nitrile solvent of the present invention (preferably, acetonitrile; more preferably, aqueous acetonitrile) is preferred in an industrial aspect to tert-butanol, which is a specific and most preferable reaction solvent in JP 2013-512201 A (Patent Document 2). For example, the solvent system of the present invention was found to be superior to the solvent system of the prior art (Patent Document 2) in terms of the stability of the solvent, the effective use of hydrogen chloride produced in the chlorination step as an acid catalyst in the next step, the viscosity and uniformity of the reaction mixture, the potential of causing clogging of a reflux condenser or a pipeline in a plant, etc.

From the same viewpoints as described above, in one embodiment, the amount of the nitrile solvent to be used in the reaction of the step (C) is generally 0.1 to 5.0 L (liters), preferably 0.3 to 4.0 L, more preferably 0.3 to 3.0 L, further preferably 0.4 to 3.0 L, further preferably 0.4 to 2.0 L, further preferably 0.5 to 2.0 L, and further preferably 0.5 to 1.0 L based on 1 mol of the compound of the formula (3). In another embodiment, it is preferably 0.1 to 2.0 L, more preferably 0.2 to 2.0 L, further preferably 0.3 to 2.0 L, further preferably 0.3 to 1.5 L, further preferably 0.4 to 1.5 L, further preferably 0.5 to 1.5 L, and further preferably 0.5 to 1.0 L.

From the same viewpoints as described above, in one embodiment, the amount of the water solvent to be used in the reaction of the step (C) is generally 0.00 to 1.00 L, preferably 0.10 to 1.00 L, more preferably 0.10 to 0.80 L, further preferably 0.10 to 0.50 L, further preferably 0.10 to 0.40 L, further preferably 0.13 to 0.40 L, further preferably 0.15 to 0.40 L, and further preferably 0.15 to 0.33 L based on 1 mol of the compound of the formula (3), and the range of 0.13 to 0.35 L is also mentioned.

From the same viewpoint as described above, in one embodiment, the amount of water (vol %) to be used in the reaction of the step (C) is generally 0 (zero) vol % to 50 vol % or less, preferably more than 0 (zero) vol % to 50 vol % or less, more preferably 5 vol % or more and 50 vol % or less, further preferably 5 vol % or more and 40 vol % or less, further preferably 10 vol % or more and 42 vol % or less, further preferably 10 vol % or more and 40 vol % or less, further preferably 20 vol % or more and 40 vol % or less, and further preferably 20 vol % or more and 30 vol % or less of the amount of the mixed solvent of the nitrile solvent (preferably acetonitrile) and water. A range of 10% vol to 30 vol % is also mentioned.

(Reaction Temperature in Step (C))

The reaction temperature of the step (C) is not particularly limited. From the viewpoints of yield, suppression of by-products, economic efficiency, etc., in one embodiment, the reaction temperature may be, for example, in the range of −30° C. (minus 30° C.) to 160° C., preferably −10° C. to 80° C., more preferably −10° C. to 40° C., further preferably −5° C. to 30° C., and further more preferably 0° C. to 30° C. From the same viewpoint as described above, in another embodiment, the reaction temperature may be, for example, preferably −5° C. to 50° C., more preferably −5° C. to 40° C., further preferably 0° C. to 40° C., and further more preferably 0° C. to 30° C.

(Reaction Time in Step (C))

The reaction time in the step (C) is not particularly limited. From the viewpoints of yield, suppression of by-products, economic efficiency, etc., in one embodiment, the reaction time may be, for example, in the range of 0.5 hours to 48 hours, preferably 0.5 hours to 24 hours, and more preferably 1 hour to 12 hours.

(Product in Step (C); Compound of Formula (4))

The product in the step (C) is a compound of the formula (4), in which the isoxazoline ring of the compound of the formula (3) used as a raw material is halogenated at the 3-position thereof.

Preferable specific examples of the compound of the formula (4) include the following, but are not limited thereto; 3-chloro-5,5-dimethyl-4,5-dihydroisoxazole, 3-bromo-5,5-dimethyl-4,5-dihydroisoxazole, 3-chloro-5-ethyl-5-methyl-4,5-dihydroisoxazole, 3-bromo-5-ethyl-5-methyl-4,5-dihydroisoxazole, 3-chloro-5,5-diethyl-4,5-dihydroisoxazole, and 3-bromo-5,5-diethyl-4,5-dihydroisoxazole.

From the viewpoints of economic efficiency, usefulness of the product, etc., more preferable specific examples of the compound of the formula (4) include 3-chloro-5,5-dimethyl-4,5-dihydroisoxazole, 3-chloro-5-ethyl-5-methyl-4,5-dihydroisoxazole, and 3-chloro-5,5-diethyl-4,5-dihydroisoxazole, and further preferably 3-chloro-5,5-dimethyl-4,5-dihydroisoxazole. The compound of the formula (4), which is the product in the step (C), can be used as a raw material in the step (D).

(Step (D))

The step (D) will be described.

The reaction in the step (D) is isothiouronium formation.

The step (D) is a step of producing a (4,5-dihydroisoxazol-3-yl)]thiocarboxamidine salt compound of the formula (5) (i.e., an isothiouronium compound) by reacting a compound of the formula (4) with an isothiouronium-forming agent. "Isothiouronium" is also referred to as "isothiuronium".

[Chemical Formula 31]

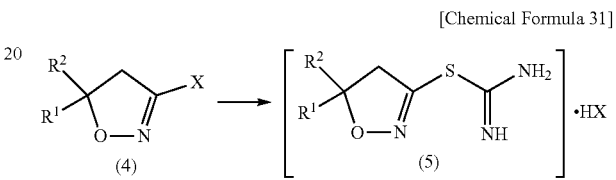

In the formula, $R^1$, $R^2$ and X are as defined above.

(Raw Material of Step (D); Compound of Formula (4))

The compound of the formula (4) is used as a raw material for the process of the present invention. The compound of the formula (4) may be a known compound or may be produced from a known compound according to a known process. In addition, the compound of the formula (4) can be produced by the process of the above step (C). In this case, the compound of the formula (4) may be used for the next step after being isolated in the step (C), or may be used for the next step after further purification, or may be used for the next step without isolation.

When the compound of the formula (4) is not isolated or purified in the step (C), the step (D) may be performed in the same reaction vessel in which the step (C) was performed.

Specific examples, preferable specific examples, more preferable specific examples, and further preferable specific examples of the compound of the formula (4) are as described above.

(Isothiouronium-forming Agent in Step (D))

The isothiouronium-forming agent used in step (D) may be any isothiouronium-forming agent as long as the reaction proceeds. However, as the isothiouronium-forming agent to be used in the step (D), thiourea is commonly used.

When thiourea is used as the isothiouronium-forming agent in the step (D), the amount of the thiourea used may be any amount as long as the reaction proceeds. From the viewpoints of yield, suppression of by-products, economic efficiency, etc., in one embodiment, the amount of the thiourea used may be, for example, in the range of 0.5 to 2.0 mol, preferably 0.9 to 1.5 mol, and more preferably 1.0 to 1.2 mol based on 1 mol of the compound of the formula (4). Also when an isothiouronium-forming agent other than thiourea is used, the same examples of the amount thereof can be mentioned.

(Solvent in Step (D))

From the viewpoints of smooth progress of the reaction, etc., it is preferable to perform the reaction of the step (D) in the presence of a solvent. When the step (D) is performed in the same reaction vessel in which the step (C) was performed, no solvent may be further added, or a solvent may be added. Further, when the reaction mixture of the step (C) is transferred to another reaction vessel and then the reaction of the step (D) is performed without isolating the compound of the formula (4), no solvent may be further added, or a solvent may be added. In any case, any solvent may be added as long as the reaction in the step (D) proceeds. Further, a part or the whole of the solvent used in the step (C) may be removed between the step (C) and the step (D) as long as the reaction proceeds. The amount of the solvent to be removed is not particularly limited. When the step (D) is performed after the compound of the formula (4) is isolated or purified in the step (C), the solvent in the step (D) may be any solvent as long as the reaction proceeds.

As to the reaction solvent in the step (D), examples of the solvent that can be used in any case described above include, but are not limited to, nitriles (e.g., acetonitrile and propionitrile); water; alcohols (e.g., methanol, ethanol, and 2-propanol); ethers (e.g., tetrahydrofuran (THF), 1,4-dioxane, diisopropyl ether, dibutyl ether, di-tert-butyl ether, cyclopentyl methyl ether (CPME), methyl-tert-butyl ether, 1,2-dimethoxyethane (DME), diglyme, and triglyme); amides (e.g., N,N-dimethylformamide (DMF), N,N-dimethylacetamide (DMAC), and N-methylpyrrolidone (NMP)); alkyl ureas (e.g., N,N'-dimethylimidazolidinone (DMI)); sulfoxides (e.g., dimethylsulfoxide (DMSO)); carboxylic acid esters (e.g., ethyl acetate and butyl acetate); aromatic hydrocarbon derivatives (e.g., benzene, toluene, xylene, chlorobenzene, and dichlorobenzene); and halogenated aliphatic hydrocarbons (e.g., dichloromethane, chloroform, and dichloroethane), and any combination thereof in any ratio. The amount of the reaction solvent used in the step (D) may be any amount as long as the reaction system can be sufficiently stirred. When a combination of two or more solvents is used, the ratio thereof may be any ratio as long as the reaction proceeds. As long as the reaction proceeds, the solvent either may form a single layer or may be separated into two layers, but preferably forms a uniform single layer.

However, from the viewpoints of smooth progress of the reaction, economic efficiency, etc., preferable examples and more preferable examples of the solvent in the step (D) are the same as those in the step (C). In these cases, preferable examples, more preferable examples, and further preferable examples of the amounts of the solvents to be used in the step (D) (that is, the amounts of the nitrile solvent and the water solvent) are the same as those in the step (C). In addition, preferable examples, more preferable examples, and even more preferable examples of the amount of water (vol %) based on the amount of the mixed solvent of the nitrile solvent (preferably acetonitrile) and water are the same as those in the step (C).

Furthermore, from the same viewpoints as described above, in one embodiment, the reaction of the step (C) and the reaction of the step (D) are preferably performed in the same solvent, but are not limited to this mode.

(Reaction Temperature in Step (D))

The reaction temperature in the step (D) is not particularly limited. From the viewpoints of yield, suppression of by-products, economic efficiency, etc., in one embodiment, the reaction temperature may be, for example, in the range of −30° C. (minus 30° C.) to 160° C., preferably −10° C. to 80° C., more preferably 0° C. to 40° C., even more preferably 10° C. to 40° C., further preferably 10° C. to 30° C., and further more preferably 15° C. to 30° C. From the same viewpoints as described above, in another embodiment, the reaction temperature may be, for example, preferably in the range of 0° C. to 80° C., more preferably 0° C. to 60° C., further preferably 15° C. to 60° C., and further more preferably 15° C. to 40° C.

(Reaction Time in Step (D))

The reaction time in the step (D) is not particularly limited. From the viewpoints of yield, suppression of by-products, economic efficiency, etc., in one embodiment, the reaction time may be, for example, in the range of 0.5 hours to 48 hours, preferably 0.5 hours to 24 hours, more preferably 1 hour to 12 hours, and even more preferably 1 hour to 8 hours.

(Product in Step (D); Compound of Formula (5))

The product in the step (D) is a thiocarboxamidine salt compound of the formula (5) (i.e., an isothiouronium compound) corresponding to the compound of the formula (4) used as a raw material.

Preferable specific examples of compound of the formula (4) include the following, but are not limited thereto; [5,5-dimethyl(4,5-dihydroisoxazol-3-yl)]thiocarboxamidine hydrochloride, [5,5-dimethyl(4,5-dihydroisoxazol-3-yl)]thiocarboxamidine hydrobromide, [5-ethyl-5-methyl(4,5-dihydroisoxazol-3-yl)]thiocarboxamidine hydrochloride, [5-ethyl-5-methyl(4,5-dihydroisoxazol-3-yl)]thiocarboxamidine hydrobromide, [5,5-diethyl(4,5-dihydroisoxazol-3-yl)]thiocarboxamidine hydrochloride, and [5,5-diethyl(4,5-dihydroisoxazol-3-yl)]thiocarboxamidine hydrobromide.

From the viewpoints of economic efficiency, usefulness of the product, etc., more preferable specific examples of the compound of the formula (4) are [5,5-dimethyl(4,5-dihydroisoxazol-3-yl)]thiocarboxamidine hydrochloride, [5-ethyl-5-methyl(4,5-dihydroisoxazol-3-yl)]thiocarboxamidine hydrochloride, [5,5-diethyl(4,5-dihydroisoxazol-3-yl)]thiocarboxamidine hydrochloride, and more preferably [5,5-dimethyl(4,5-dihydroisoxazol-3-yl)]thiocarboxamidine hydrochloride.

Unless otherwise indicated, it is understood that numbers used herein to express characteristics such as quantities, sizes, concentrations, and reaction conditions are modified by the term "about". In some embodiments, disclosed numerical values are interpreted applying the reported number of significant digits and conventional rounding techniques. In some embodiments, disclosed numerical values are interpreted as containing certain errors necessarily resulting from the standard deviation found in their respective testing measurements.

Hereinafter, the present invention will be described in more detail by Examples, but the present invention is not limited in any way by these Examples.

Herein, the following instruments and conditions were used for the analysis in the examples and comparative examples.

($^1$H-NMR: $^1$H nuclear magnetic resonance spectrum)

Instrument: JEOL JMN-ECS-300 or JEOL JMN-Lambda-400 (manufactured by JEOL RESONANCE Ltd.), solvent: CDCl$_3$ and/or DMSO-d$_6$, internal standard substance: tetramethylsilane (TMS) and others.

(GC Analysis: Gas Chromatography Analysis)

GC-2025 (manufactured by Shimadzu Corporation), detection method: FID

Gas chromatography (GC) analysis method; regarding the GC analysis method, the following documents can be referred to, if necessary.

Document (a): "Shin-Jikkenkagaku Koza 9, Bunseki Kagaku II (A New Course in Experimental Chemistry 9, Analytical Chemistry II)", pp. 60 to 86 (1977), edited by The Chemical Society of Japan, published by Shingo Iizumi, Maruzen Co., Ltd. (for example, page 66 of this document can be referred to with respect to liquids for a stationary phase to be usable for a column).

Document (b): "Jikkenkagaku Koza 20-1, Bunseki Kagaku (A Course in Experimental Chemistry 20-1, Analytical Chemistry)", 5th edition, pp. 121 to 129 (2007), edited by The Chemical Society of Japan, published by Seishiro Murata, Maruzen Co., Ltd. (for example, pages 124 to 125 of this document can be referred to with respect to the specific usage of hollow capillary separation columns).

(GC-MS Analysis: Gas Chromatography Mass Spectrometry Analysis)

Analysis instrument: 6890N Network GC System (manufactured by Agilent Technologies), mass detector: 5973N MSD (manufactured by Agilent Technologies)

Herein, room temperature and ambient temperature are from 15° C. to 30° C.

Example 1

Production of [5,5-dimethyl(4,5-dihydroisoxazol-3-yl)]thiocarboxamidine hydrochloride (5-a)

Step (C; Chlorination) and Step (D; Formation of Isothiouronium)

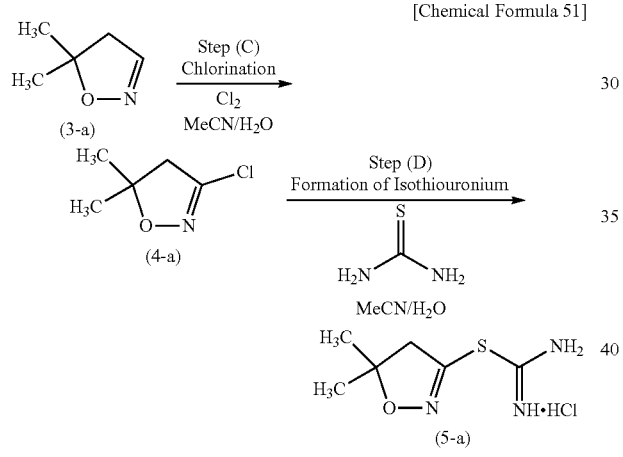

[Chemical Formula 51]

(1) Production of 3-chloro-5,5-dimethyl-4,5-dihydroisoxazole (4-a)

Step (C; Chlorination)

5,5-Dimethyl-4,5-dihydroisoxazole (3-a; 186 mg, 1.88 mmol, 100 mol %) was dissolved in acetonitrile (0.94 ml, 0.5 L (liters)/mol, based on (3-a)) and water (0.28 ml, 0.15 L/mol, based on (3-a)). Chlorine gas (50 ml as gas, measured with a gas tight syringe at 25° C., gas specific gravity: 2.935 g/L (liter) (25° C.), 0.147 g, 2.07 mmol, 110 mol %) was introduced thereto at 25 to 30° C., and the mixture was stirred at the same temperature for 1 hour. The GC-MS analysis of the reaction mixture confirmed the formation of the target 3-chloro-5,5-dimethyl-4,5-dihydroisoxazole (4-a). As a result of the GC analysis (area percentage) of the reaction mixture, the components in the reaction mixture excluding the solvents and the like were as follows:

3-chloro-5,5-dimethyl-4,5-dihydroisoxazole (4-a; target intermediate): 99%.

(2) Production of [5,5-dimethyl(4,5-dihydroisoxazol-3-yl)]thiocarboxamidine hydrochloride (5-a)

Step (D; Formation of Isothiouronium)

Then, thiourea (143 mg, 1.88 mmol, 100 mol %) was added thereto, and the mixture was stirred at room temperature for 15 hours. After the completion of the reaction, the reaction mixture was concentrated under reduced pressure to obtain [5,5-dimethyl(4,5-dihydroisoxazol-3-yl)]thiocarboxamidine hydrochloride (5-a; 386 mg, 1.84 mmol, yield: 98%).

$^1$H-NMR (400 MHz, CDCl$_3$-DMSO-d$_6$) δ(ppm, relative to TMS): 1.48 (s, 6H), 2.99 (s, 2H), 9.63 (bs, 2H), 9.88 (bs, 2H).

Examples 2 to 21 and Comparative Example 1

Production of 3-chloro-5,5-dimethyl-4,5-dihydroisoxazole (4-a)

Step (C; Chlorination)

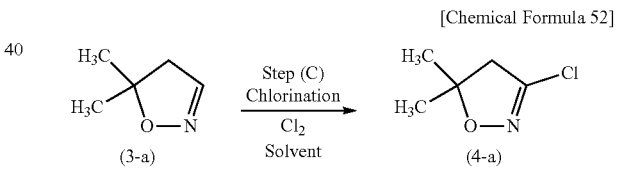

[Chemical Formula 52]

The chlorination in the step (C) was performed in the same manner as in Example 1 (1) except that the solvent was changed as shown in Table 1 below. The results of the GC analysis (area percentage) of the reaction mixture are shown in Table 1 below for the target product, the raw material, and other by-products. In addition, Table 1 also shows the result of Example 1 (1).

TABLE 1

| Example | Nitrile solvent (L/mol) | | Water (L/mol) | Amount Water Contained in Solvent (vol %) | Uniformity | Ratio in Reaction Mixture (%) | | |
|---|---|---|---|---|---|---|---|---|
| | | | | | | (4-a) Target Product | (3-a) Raw Material | By-products |
| Example 2 | CH$_3$CN | 1.00 | 0 | 0 | ○ | 94 | 1 | 5 |
| Example 3 | CH$_3$CN | 1.00 | 0.09 | 8 | ○ | 93 | 0 | 7 |
| Example 4 | CH$_3$CN | 1.00 | 0.15 | 13 | ○ | 97 | 0 | 3 |
| Example 5 | CH$_3$CN | 1.00 | 0.33 | 25 | ○ | 97 | 2 | 1 |
| Example 6 | CH$_3$CN | 1.00 | 0.50 | 33 | x | 90 | 6 | 4 |
| Example 7 | CH$_3$CN | 0.50 | 0 | 0 | ○ | 90 | 0 | 10 |

TABLE 1-continued

| Example | Nitrile solvent (L/mol) | | Water (L/mol) | Amount Water Contained in Solvent (vol %) | Uniformity | Ratio in Reaction Mixture (%) | | |
|---|---|---|---|---|---|---|---|---|
| | | | | | | (4-a) Target Product | (3-a) Raw Material | By-products |
| Example 8 | CH$_3$CN | 0.50 | 0.06 | 10 | ○ | 61 | 0 | 39 |
| Example 9 | CH$_3$CN | 0.50 | 0.10 | 17 | ○ | 77 | 1 | 22 |
| Example 1 | CH$_3$CN | 0.50 | 0.15 | 23 | ○ | 99 | 1 | 0 |
| Example 10 | CH$_3$CN | 0.50 | 0.20 | 29 | ○ | 99 | 0 | 1 |
| Example 11 | CH$_3$CN | 0.50 | 0.33 | 40 | ○ | 99 | 0 | 1 |
| Example 12 | CH$_3$CN | 0.50 | 0.40 | 44 | x | 84 | 13 | 3 |
| Example 13 | CH$_3$CN | 0.50 | 0.50 | 50 | x | 84 | 12 | 4 |
| Example 14 | CH$_3$CN | 0.35 | 0.15 | 30 | x | 84 | 2 | 14 |
| Example 15 | CH$_3$CN | 0.30 | 0.20 | 40 | x | 79 | 5 | 16 |
| Example 16 | CH$_3$CN | 0.20 | 0 | 0 | ○ | 88 | 0 | 12 |
| Example 17 | C$_2$H$_5$CN | 0.50 | 0 | 0 | ○ | 89 | 0 | 11 |
| Example 18 | C$_2$H$_5$CN | 0.50 | 0.10 | 17 | x | 91 | 0 | 9 |
| Example 19 | C$_2$H$_5$CN | 0.50 | 0.20 | 29 | x | 93 | 2 | 5 |
| Example 20 | C$_2$H$_5$CN | 0.50 | 0.40 | 44 | x | 80 | 14 | 6 |
| Example 21 | C$_2$H$_5$CN | 0.20 | 0 | 0 | ○ | 82 | 0 | 18 |
| Comparative Example 1 | CH$_3$CN | 0 | 0.50 | 100 | x | 45 | 47 | 8 |

Uniformity ○: The reaction mixture was uniform.
Uniformity x: The reaction mixture separated into two layers.

When only the nitrile solvent was used as the reaction solvent, the reaction proceeded. However, by-products were also formed (see Examples 2, 7, 16, 17 and 21). On the other hand, when only water was used as the reaction solvent, the yield was as low as 45% (see Comparative Example 1). Even in the presence of the nitrile solvent and the water solvent, though the reaction proceeded, there were some examples in which the yield was low because a large number of small amounts of impurities were produced as by-products (see Examples 8, 9, 14, 15, and 18). Surprisingly, however, in the presence of an appropriate amount of the nitrile solvent and an appropriate amount of the water solvent, extremely high yields were achieved with reduced formation of impurities (by-products). This surprising effect was particularly observed when the nitrile solvent was acetonitrile (CH$_3$CN), and very satisfactory yields were obtained (see Examples 1, 4, 5, 10 and 11). Further, according to the process of the present invention, an extremely high yield was achieved in the step (D) in a short time (see Example 1 (2)).

Example 22

Production of 3-chloro-5,5-dimethyl-4,5-dihydroisoxazole (4-a)

Step (C; Chlorination)

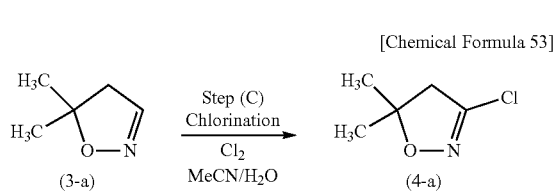

[Chemical Formula 53]

5,5-Dimethyl-4,5-dihydroisoxazole (3-a; 5.0 g, 50.4 mmol, 100 mol %) was dissolved in acetonitrile (25 ml, 0.5 L (liters)/mol, based on (3-a)) and water (10 ml, 0.2 L/mol, based on (3-a)). While stirring with a magnetic stirrer, chlorine gas (2.6 ml, liquefied at −70° C. and measured, specific gravity: 1.64 (−70° C.), 4.3 g, 60.5 mmol, 120 mol %) was introduced thereto at 2 to 5° C. over 30 minutes, and the mixture was stirred at the same temperature for 1 hour. As a result of the GC analysis (area percentage) of the reaction mixture, the components in the reaction mixture excluding the solvents and the like were as follows:
3-chloro-5,5-dimethyl-4,5-dihydroisoxazole (4-a; target product): 98%.

After the completion of the reaction, ethyl acetate (25 ml), a 1 M sodium thiosulfate (Na$_2$S$_2$O$_3$) aqueous solution (5 ml) and a saturated sodium chloride aqueous solution (10 ml) were added to the reaction mixture, and the mixture was stirred. The organic layer and the aqueous layer were separated from each other, so that the organic layer was obtained. The organic layer was washed with a small amount of a saturated sodium hydrogen carbonate (NaHCO$_3$) aqueous solution and then was concentrated under reduced pressure until the volume of the organic layer was reduced to about 10 ml. Dichloromethane (25 ml) was added thereto, and the organic layer was dried over magnesium sulfate and concentrated under reduced pressure. The resultant crude product was purified by distillation to obtain 3-chloro-5,5-dimethyl-4,5-dihydroisoxazole (4-a, colorless oil, 5.8 g, purity: 99.9% (GC area percentage), 43.4 mmol, yield: 86%, boiling point: 70 to 72° C./20 Torr).
$^1$H-NMR (400 MHz, CDCl$_3$) δ(ppm, relative to TMS): 1.46 (s, 6H), 2.93 (s, 2H).

Example 23

Production of [5,5-dimethyl(4,5-dihydroisoxazol-3-yl)]thiocarboxamidine hydrochloride (5-a)

Step (C; Chlorination) and Step (D; Formation of Isothiouronium)

[Chemical Formula 54]

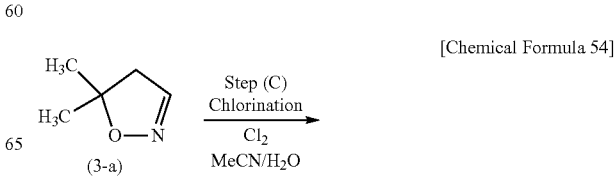

23

-continued

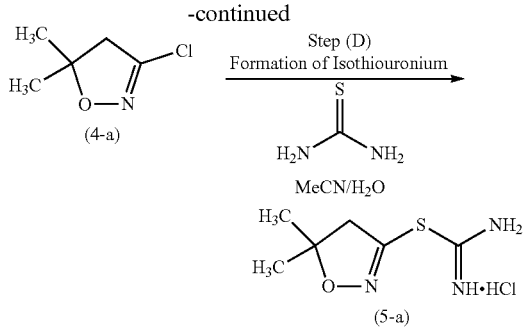

(1) Production of
3-chloro-5,5-dimethyl-4,5-dihydroisoxazole (4-a)

Step (C; Chlorination)

5,5-Dimethyl-4,5-dihydroisoxazole (3-a; 10.0 g, 101 mmol, 100 mol %) was dissolved in acetonitrile (50 ml, 0.5 L (liters)/mol, based on (3-a)) and water (20 ml, 0.2 L/mol, based on (3-a)). While stirring with a magnetic stirrer, chlorine gas (5.2 ml, liquefied at −70° C. and measured, specific gravity: 1.64 (−70° C.), 8.6 g, 121 mmol, 120 mol %) was introduced thereto at 2 to 5° C. over 1 hour, and the mixture was stirred at the same temperature for 1 hour. As a result of the GC analysis (area percentage) of the reaction mixture, the components in the reaction mixture excluding the solvents and the like were as follows:

3-chloro-5,5-dimethyl-4,5-dihydroisoxazole (4-a; target intermediate): 98%.

(2) Production of [5,5-dimethyl(4,5-dihydroisoxazol-3-yl)]thiocarboxamidine hydrochloride (5-a)

Step (D; Formation of Isothiouronium)

Then, thiourea (8.5 g, 111 mmol, 110 mol %) was added thereto, and the mixture was stirred at 30° C. for 7 hours. The NMR analysis of the reaction mixture confirmed the formation of the target [5,5-dimethyl(4,5-dihydroisoxazol-3-yl)]thiocarboxamidine hydrochloride (5-a). The conversion of 3-chloro-5,5-dimethyl-4,5-dihydroisoxazole (4-a) to [5,5-dimethyl(4,5-dihydroisoxazol-3-yl)]thiocarboxamidine hydrochloride (5-a) was 90% at 4 hours after the addition of thiourea, and 99% at 7 hours after the addition of thiourea. Acetamide and acetic acid, which could be formed by decomposition of acetonitrile used as a solvent, were not observed. After the completion of the reaction, the reaction mixture was concentrated under reduced pressure. The operation of adding ethanol (20 ml) and toluene (80 ml) and concentrating the mixture was performed twice, the resultant crude solid was dissolved in isopropyl alcohol (100 ml), insolubles were removed by filtration, and the resultant filtrate was concentrated under reduced pressure. The resultant solid was collected by filtration and washed with ethyl acetate to obtain [5,5-dimethyl(4,5-dihydroisoxazol-3-yl)]thiocarboxamidine hydrochloride (5-a; colorless solid, 17.5 g, 83.5 mmol, yield: 83%).

$^1$H-NMR (400 MHz, $CDCl_3$-DMSO-$d_6$) δ(ppm, relative to TMS): 1.48 (s, 6H), 2.99 (s, 2H), 9.63 (bs, 2H), 9.88 (bs, 2H).

24

Comparative Example 2

Production of [5,5-dimethyl(4,5-dihydroisoxazol-3-yl)]thiocarboxamidine hydrochloride (5-a) Using Tert-Butanol as Reaction Solvent Step (C; Chlorination) and Step (D; Formation of Isothiouronium)

[Chemical Formula 54]

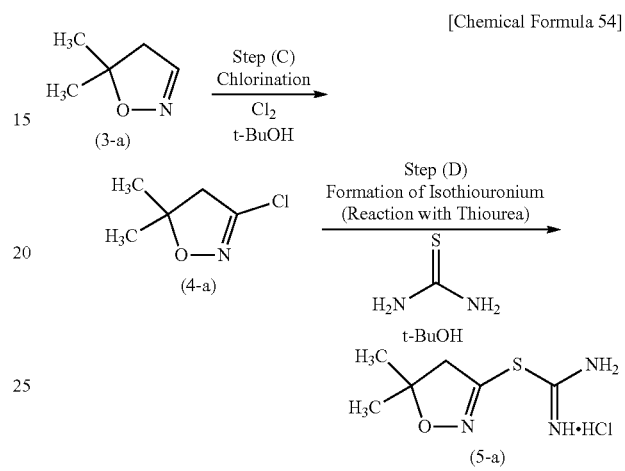

(1) Production of
3-chloro-5,5-dimethyl-4,5-dihydroisoxazole (4-a)

Step (C; Chlorination)

5,5-Dimethyl-4,5-dihydroisoxazole (3-a; 10.0 g, 101 mmol, 100 mol %) was dissolved in tert-butanol (20 ml, 0.2 L (liters)/mol, based on (3-a), the same amount of tert-butanol as in Example 6 of JP 2013-512201 A (Patent Document 2) was used). While stirring with a magnetic stirrer, chlorine gas (5.2 ml, liquefied at −70° C. and measured, specific gravity: 1.64 (−70° C.), 8.6 g, 121 mmol, 120 mol %) was introduced thereto at 20 to 25° C. over 1 hour, and the mixture was stirred at the same temperature for 1 hour. As a result of the GC analysis (area percentage) of the reaction mixture, the components in the reaction mixture excluding the solvents and the like were as follows:

3-chloro-5,5-dimethyl-4,5-dihydroisoxazole (4-a; target intermediate): 98%.

(2) Production of [5,5-dimethyl(4,5-dihydroisoxazol-3-yl)]thiocarboxamidine hydrochloride (5-a)

Step (D; Formation of Isothiouronium)

Then, thiourea (8.5 g, 111 mmol, 110 mol %) was added thereto, and the mixture was stirred at 30° C. After 1 hour, a white solid presumed to be [5,5-dimethyl(4,5-dihydroisoxazol-3-yl)]thiocarboxamidine hydrochloride (5-a) precipitated, so that it became impossible to continue stirring. The NMR analysis of the reaction mixture revealed that the conversion of 3-chloro-5,5-dimethyl-4,5-dihydroisoxazole (4-a) to [5,5-dimethyl(4,5-dihydroisoxazol-3-yl)]thiocarboxamidine hydrochloride (5-a) was 63%. At this point, 15% of the theoretical amount of hydrogen chloride generated in the previous step had been converted to tert-butyl chloride by the reaction with tert-butanol. The amount of tert-butyl chloride was calculated from the ratio of the peak area derived from methyl of tert-butyl chloride to the peak area derived from methyl on the isoxazoline ring of the target product (5-a).

tert-Butanol (50 ml, 0.5 L (liters)/mol, based on (3-a)) was added thereto, and after confirming that the mixture was stirred, the reaction was continued. Seven hours after the addition of thiourea, a portion of the reaction mixture was sampled and analyzed by NMR. As a result, the conversion of 3-chloro-5,5-dimethyl-4,5-dihydroisoxazole (4-a) to [5,5-dimethyl(4,5-dihydroisoxazol-3-yl)]thiocarboxamidine hydrochloride (5-a) was 86%. At this point, 49% of the theoretical amount of hydrogen chloride generated in the previous step had been converted to tert-butyl chloride.

INDUSTRIAL APPLICABILITY

The (4,5-dihydroisoxazol-3-yl)thiocarboxamidine salt compound of the formula (5) produced by the process of the present disclosure is useful as an intermediate for producing pharmaceuticals and agricultural chemicals, particularly, a herbicide pyroxasulfone. According to the present disclosure, the target compound can be produced in a short time and with a high yield. According to the present disclosure, it is possible to produce the target compound by a simple operation without requiring a special equipment. Therefore, the process of the present disclosure is industrially preferable, economical, and environmentally friendly, and has high industrial utility value. In short, the present disclosure has a high industrial applicability.

The invention claimed is:

1. A process for producing a compound of the formula (5):

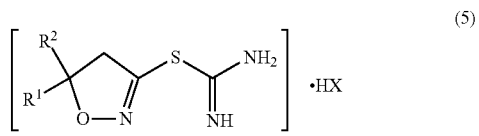

(5)

wherein $R^1$ and $R^2$ are each independently optionally substituted (C1-C6)alkyl; optionally substituted (C3-C6)cycloalkyl; optionally substituted (C2-C6)alkenyl; optionally substituted (C2-C6)alkynyl; optionally substituted (C1-C6)alkoxy; or optionally substituted phenyl; or $R^1$ and $R^2$, together with the carbon atom to which they are attached form a 4- to 12-membered carbocyclic ring, wherein the formed ring is optionally substituted, X is a halogen, which comprises the following steps (C) and (D):

step (C): reacting a compound of the formula (3) with a halogenating agent in the presence of a nitrile solvent and a water solvent to produce a compound of the formula (4),

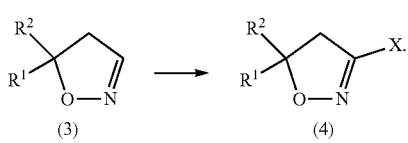

wherein $R^1$, $R^2$ and X are as defined above, step (D): reacting the compound of the formula (4) with an isothiouronium-forming agent to produce the compound of the formula (5),

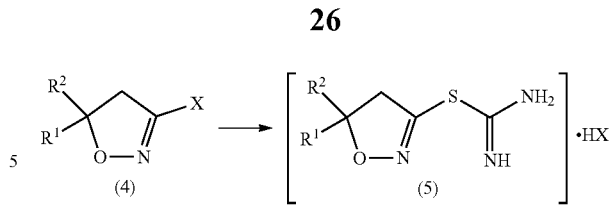

wherein $R^1$, $R^2$ and X are as defined above.

2. The process according to claim 1, wherein the amount of the nitrile solvent to be used in the reaction of the step (C) is 0.4 to 2.0 L based on 1 mol of the compound of the formula (3).

3. The process according to claim 1, wherein the amount of the nitrile solvent to be used in the reaction of the step (C) is 0.5 to 1.5 L based on 1 mol of the compound of the formula (3).

4. The process according to claim 1, wherein the amount of the nitrile solvent to be used in the reaction of the step (C) is 0.5 to 1.0 L based on 1 mol of the compound of the formula (3).

5. The process according to claim 1, wherein the amount of the water solvent to be used in the reaction of the step (C) is 0.10 to 0.40 L based on 1 mol of the compound of the formula (3).

6. The process according to claim 1, wherein the amount of the water solvent to be used in the reaction of the step (C) is 0.15 to 0.33 L based on 1 mol of the compound of the formula (3).

7. The process according to claim 1, wherein the amount of water to be used in the reaction of the step (C) is 10 vol % or more and 42 vol % or less of the amount of the mixed solvent of the nitrile solvent and water.

8. The process according to claim 1, wherein the amount of water to be used in the reaction of the step (C) is 10 vol % or more and 40 vol % or less of the amount of the mixed solvent of the nitrile solvent and water.

9. The process according to claim 1, wherein the amount of water to be used in the reaction of the step (C) is 20 vol % or more and 40 vol % or less of the amount of the mixed solvent of the nitrile solvent and water.

10. The process according to claim 1, wherein the reaction of the step (D) is performed in the presence of a nitrile solvent.

11. The process according to claim 1, wherein the reaction of the step (D) is performed in the presence of a nitrile solvent and a water solvent.

12. The process according to claim 10, wherein the amount of the nitrile solvent to be used in the reaction of the step (D) is 0.4 to 2.0 L based on 1 mol of the compound of the formula (3).

13. The process according to claim 10, wherein the amount of the nitrile solvent to be used in the reaction of the step (D) is 0.5 to 1.5 L based on 1 mol of the compound of the formula (3).

14. The process according to claim 10, wherein the amount of the nitrile solvent to be used in the reaction of the step (D) is 0.5 to 1.0 L based on 1 mol of the compound of the formula (3).

15. The process according to claim 11, wherein the amount of the water solvent to be used in the reaction of the step (D) is 0.10 to 0.40 L based on 1 mol of the compound of the formula (3).

16. The process according to claim 11, wherein the amount of the water solvent to be used in the reaction of the step (D) is 0.15 to 0.33 L based on 1 mol of the compound of the formula (3).

17. The process according to claim 11, wherein the amount of water to be used in the reaction of the step (D) is 10 vol % or more and 42 vol % or less of the amount of the mixed solvent of the nitrile solvent and water.

18. The process according to claim 11, wherein the amount of water to be used in the reaction of the step (D) is 10 vol % or more and 40 vol % or less of the amount of the mixed solvent of the nitrile solvent and water.

19. The process according to claim 11, wherein the amount of water to be used in the reaction of the step (D) is 20 vol % or more and 40 vol % or less of the amount of the mixed solvent of the nitrile solvent and water.

20. The process according to claim 1, wherein the reaction of the step (C) and the reaction of the step (D) are performed in the same solvent.

21. The process according to claim 1, wherein the step (C) and the step (D) are performed in the same reaction vessel.

22. The process according to claim 1, wherein the nitrile solvent is acetonitrile.

23. The process according to claim 1, wherein the halogenating agent is chlorine.

24. The process according to claim 1, wherein the isothiouronium-forming agent is thiourea.

25. The process according to claim 1, wherein $R^1$ and $R^2$ are methyl and X is a chlorine atom.

* * * * *